US00PP19073P2

(12) United States Plant Patent
Berry

(10) Patent No.: US PP19,073 P2
(45) Date of Patent: Aug. 5, 2008

(54) INDIAN HAWTHORN PLANT NAMED 'LISTO'

(50) Latin Name: *Raphiolepis indica*
Varietal Denomination: Listo

(76) Inventor: James Bryan Berry, 25075 Austin Rd., Daphne, AL (US) 36526

( * ) Notice: Subject to any disclaimer, the term of this patent is extended or adjusted under 35 U.S.C. 154(b) by 59 days.

(21) Appl. No.: 11/297,138

(22) Filed: Dec. 8, 2005

(51) Int. Cl.
*A01H 5/00* (2006.01)

(52) U.S. Cl. ..... Plt./254

(58) Field of Classification Search ..... Plt./254
See application file for complete search history.

*Primary Examiner*—Kent L. Bell
*Assistant Examiner*—June Hwu

(57) ABSTRACT

A new and distinct variety of *Raphiolepis indica* that possesses unique color and growth habit.

1 Drawing Sheet

Latin name: *Raphiolepis indica.*
Variety denomination: 'Listo'.

BACKGROUND OF THE INVENTION

The new cultivar 'Listo' originated from a group of seed of an unknown source. Jams Berry grew the seeds in Loxley, Ala. at a commercial nursery. James Berry selected the seedling now known as 'Listo' because of the superior horticultural qualities Mr. Berry identified.

James Berry conducted asexual propagation by cuttings of 'Listo' in Loxley, Ala. at a commercial nursery. Mr. Berry determined that the plant was stable and reproduced true to form over 6 generations.

SUMMARY OF THE INVENTION

'Listo' possesses the following combination of characteristics making it unique and useful in today's landscape.

1. Very dark green foliage
2. A leathery texture and thickness of the leaves that yield a very high level of foliar leafspot resistance
3. Dense branching
4. Mounding to spreading growth habit
5. Profuse pink flowers
6. As dark or darker a pink flower than any other *Raphiolepis indica* cultivar.

BRIEF DESCRIPTION OF ILLUSTRATION

FIG. 1) This photo illustrates the unusually dark green foliage, the undulate twist of the leaf, the dense branching, and the mounding growth habit.

FIG. 2) This photo illustrates the quantity and color of the flowers and buds.

DETAILED BOTANICAL DESCRIPTION OF THE PLANT

Botanical descriptions and data were obtained from a three year old individual plant growing in #3 container at a commercial nursery using normal commercial methods. The color chart used in all descriptions was The Royal Horticultural Society Colour Chart [R.H.S.].

Plant hardiness: USDA Zone 7.
Resistance to known pathogens: Entomosporium.
Average size at 5 years: 30" high and 40" wide.
Roots: Fleshy diffuse.
Fruit:
- *Length.*—1.1 cm.
- *Width.*—1.0 cm.
- *Color.*—RHS Brown Group 200A.
- *Peduncle diameter.*—0.6 cm to 1.0 cm.
- *Type.*—Drupe.
- *Texture.*—Smooth.
- *Shape.*—Round.
- *Size.*—Average 1.4 mm diameter.
- *Seasons.*—Summer, fall and winter.
- *Color.*—RHS Brown Group 200A.

Flower:
- *Bud color.*—RHS yellow-green group 146D.
- *Bud shape.*—Prolate spheroid.
- *Average bud size.*—Length 8.8 mm. Widest part 3.0 mm.
- *Floret's shape or form.*—Florets are elliptical with obtuse tips.
- *Flower color as fading.*—The floret matures after 3 days and change to Red-Purple Group 65B, upper and under surfaces. The color further evolves after several days maturing to White Group 155B.
- *Color.*—RHS Red Purple Group 74C.
- *Form.*—Panicles 3.5" long and 2.5" wide 8 to 10 flowers per panicle.
- *Period.*—March 12$^{th}$ to March 25$^{th}$ to Loxley, Ala.
- *Petals.*—Each flower has 5 petals. They average 1 cm long and 0.5 cm wide. Petals are elliptical with obtuse tips.
- *Calyx.*—Average size is 0.5 cm diameter and 1 cm depth. The color is Greyed-Purpled Group 185A completely. The surface texture is pubescent and soft.
- *Pedicel.*—Average size is 0.4 cm long. Color is Yellow-Green Group 144B.
- *Peduncle.*—Average size range from 1.2 cm to 6.4 cm long. Color is Yellow-Green Group 144B.
- *Reproductive organs.*—Each flower has 14 to 20 stamens; 0.5 cm long; color is White Group 155C.

Anthers are Yellow-Group 10B. The pollen is Yellow Group 9C. The pistils are 0.5 cm long; color White Group 155C; each pistil has 2 styles, united with ciliate margins. Maturing pistils and stamens are Red-Purple Group 63B.

*Blooms.*—Not observed for self-cleaning characteristic or fragrance.

Leaf:

*Petiole.*—RHS Greyed Purple Group 187C.
*Base.*—Acute.
*Apices.*—Acute.
*Margin.*—Entire.
*Venation.*—Pinnate.
*Shape.*—Oblanceolate.
*Texture.*—Leathery and thick.
*Color top.*—RHS Green Group 137A.
*Winter color.*—RHS Red-purple Group 59A.
*Lower leaf surface color.*—RHS Green group 138B.
*Underside vein.*—RHS Green Group 137C.
*Underside intervein.*—RHS Green Group 143D.
*Width.*—25 mm.
*Length.*—52.4 mm.
*Petiole.*—10.6 mm.
*Petiole texture.*—Like fine sand paper.
*Internode length.*—4 cm.
*Upper surface texture.*—Leathery to the touch.
*Lower surface texture.*—Visually raised vein.
*Stipule.*—None.
*Stem color.*—RHS Brown group 200C.
*Stem texture.*—Smooth.
*Stem average length.*—3.5".

It is claimed:

1. A new and unique variety of *Raphiolepis indica* plant named *Raphiolepis* 'Listo' as herein shown and described.

* * * * *

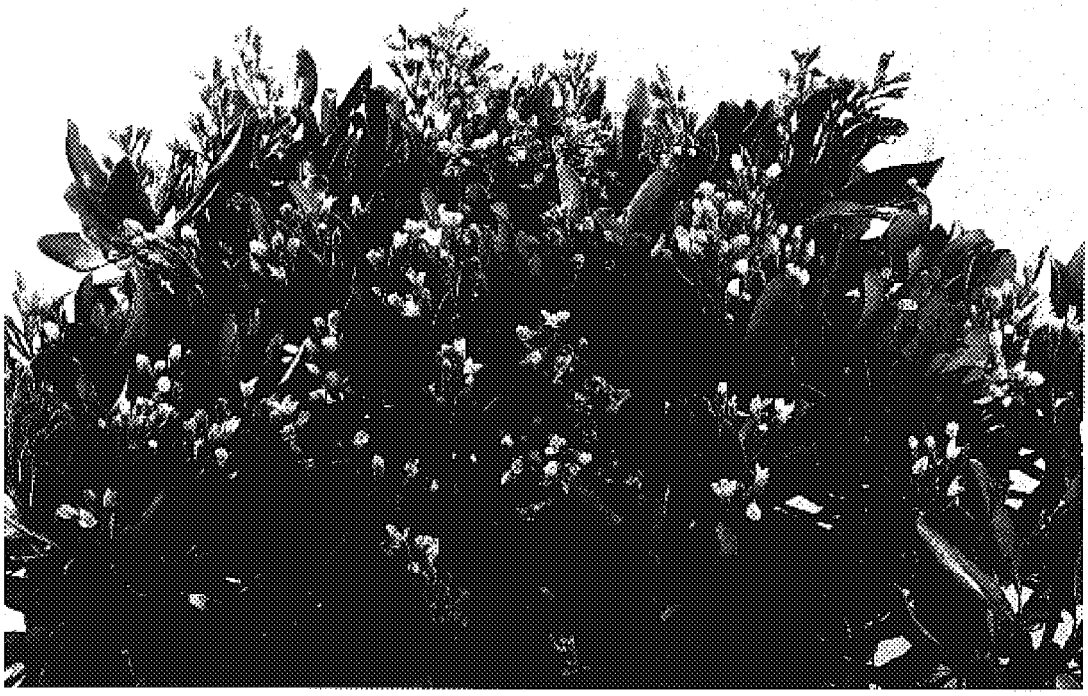
figure one
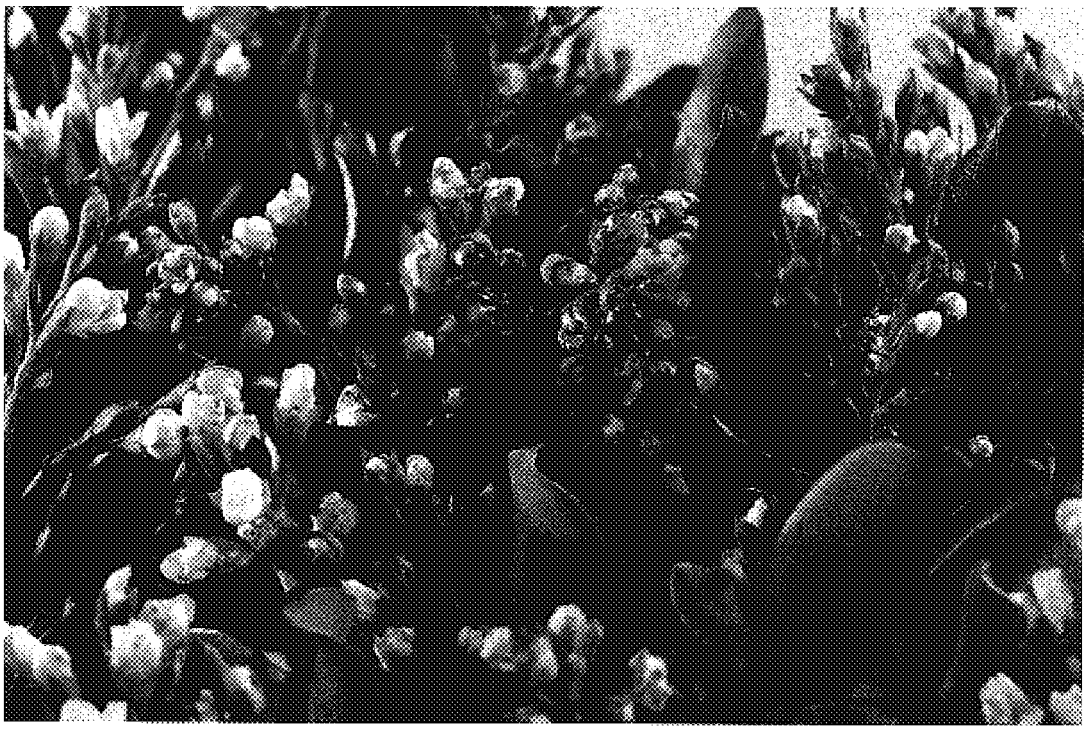
figure 2